(12) United States Patent
Lee

(10) Patent No.: US 6,606,520 B1
(45) Date of Patent: Aug. 12, 2003

(54) ROLLER TYPE HYPERTHERMO-RADIATIVE APPARATUS FOR A MAT FOR HOT COMPRESS AND ACUPRESSURE

(75) Inventor: Hwan-Sung Lee, Seoul (KR)

(73) Assignee: Ceragem International, Inc., Los Angeles, CA (US)

( * ) Notice: Subject to any disclaimer, the term of this patent is extended or adjusted under 35 U.S.C. 154(b) by 9 days.

(21) Appl. No.: 09/991,145

(22) Filed: Nov. 13, 2001

(30) Foreign Application Priority Data

Nov. 15, 2000 (KR) ........................................ 2000-67867
Dec. 4, 2000 (KR) ........................................ 2000-73144

(51) Int. Cl.⁷ ................................................ A61F 7/12
(52) U.S. Cl. ........................... 607/98; 607/96; 607/100; 601/19; 601/20
(58) Field of Search .................... 607/90, 91, 96–102, 607/154, 156; 606/201, 204, 237–245; 601/19, 20

(56) References Cited

U.S. PATENT DOCUMENTS 3,645,256 A * 2/1972 Morrison .................... 601/122
5,094,225 A * 3/1992 Craw .......................... 601/19

FOREIGN PATENT DOCUMENTS

JP 58-073237 5/1983 .......... A61H/15/00

* cited by examiner

*Primary Examiner*—Roy D. Gibson
(74) *Attorney, Agent, or Firm*—Lee & Hong

(57) ABSTRACT

The present invention, which relates to a roller type hyperthermo-radiative apparatus, is designed to minimize friction resistance upon horizontal movement thereof. The roller type hyperthermo-radiative apparatus includes a backing plate with wheels fixedly supported at four corners thereof. A plurality of pairs of supporting mechanisms is mounted on the backing plate. Roller type rotating members are rotatably installed between respective pairs of the supporting mechanism and include cylindrical empty spaces formed therein. Heating members are inserted into the empty spaces of the rotating members from both ends of the spaces. Bearing members fixedly support the heating members to the supporting means and rotatably couple the rotating members thereto. Socket portions are connected to the heating members for supplying external electric power. The roller type hyperthermo-radiative apparatus is preferably mounted on a mat for hot compress and acupressure.

15 Claims, 9 Drawing Sheets

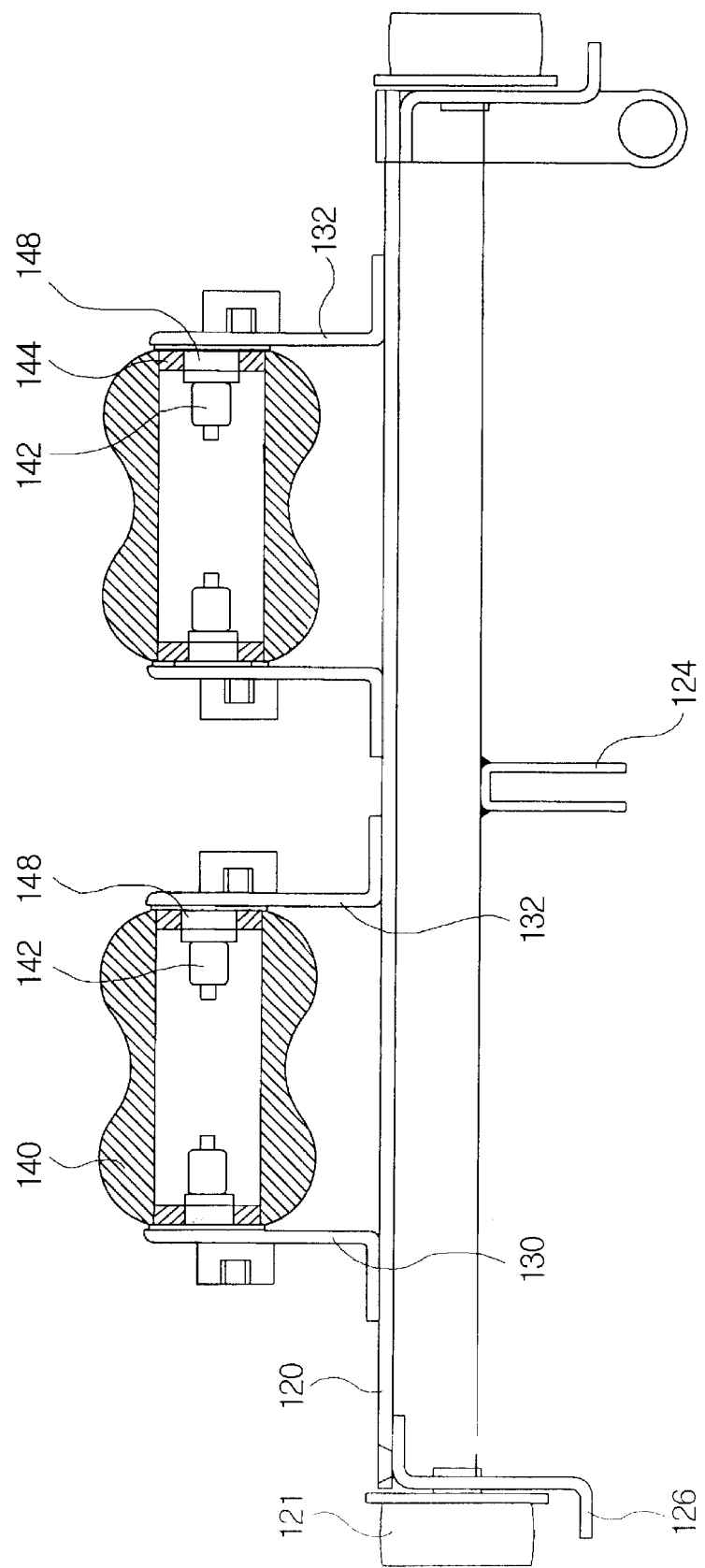

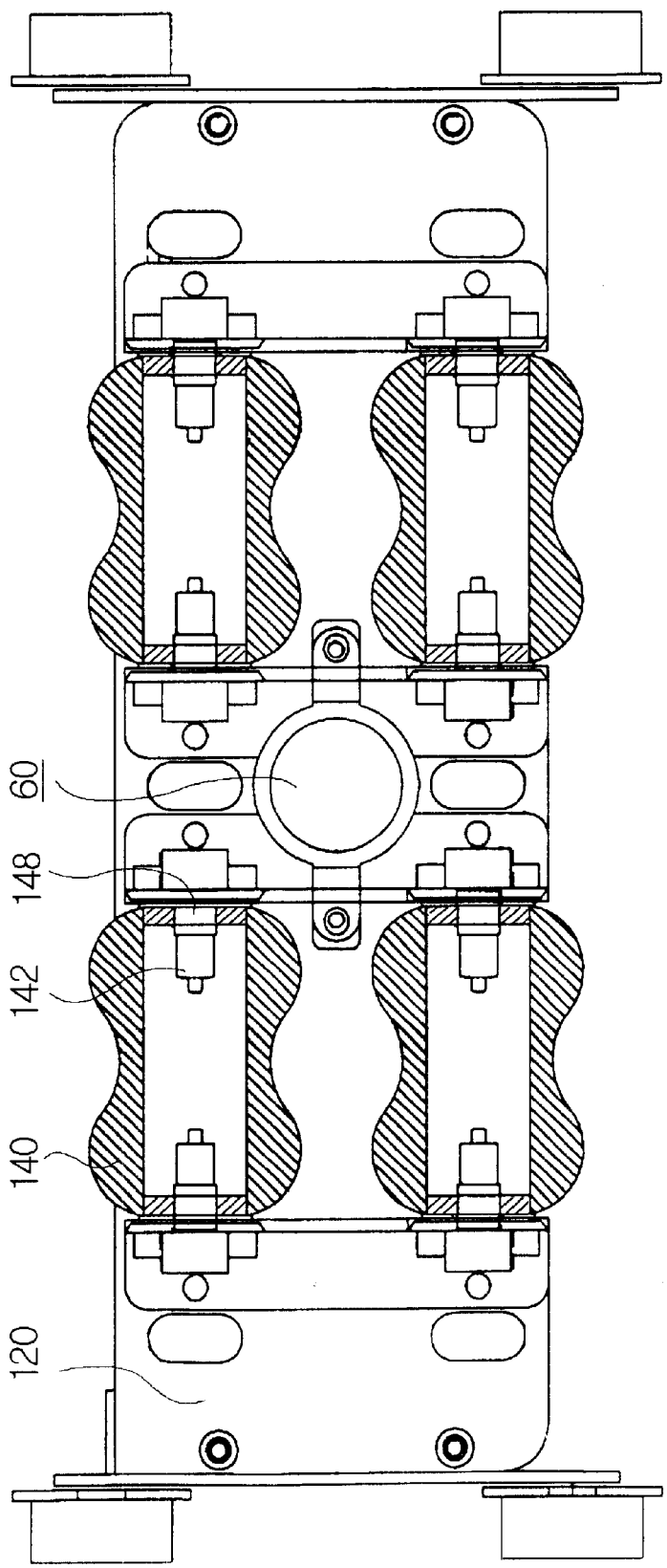

ROLLER TYPE HYPERTHERMO-RADIATIVE APPARATUS FOR A MAT FOR HOT COMPRESS AND ACUPRESSURE

BACKGROUND OF THE INVENTION

1. Field of the Invention

The present invention relates to a new type hyperthermo-radiative apparatus, more particularly, a roller type hyperthermo-radiative apparatus designed to minimize friction resistance of the apparatus upon horizontal movement thereof.

2. Description of the Prior Art

The present invention relates to improvements on the invention disclosed in Korean Patent Application No. 1999-26985 entitled "a treatment mat" (which was filed on Jan. 14, 2000 in U.S.A. and issued U.S. Pat. No. 6,243,609 on Jun. 5, 2001).

FIG. 1A shows the conventional mat for hot compress and acupressure, and FIG. 1B shows a sectional view of the conventional hyperthermo-radiative apparatus. As shown well in FIG. 1A, the conventional mat for hot compress and acupressure comprises a backing plate 50 formed on a lower side corresponding to a longitudinal groove at the center thereof, rails 51 installed on the left and right sides of the backing plate 50, a hyperthermo-radiative apparatus 60 moving horizontally along the rails 51, a horizontal moving means for causing the hyperthermo-radiative apparatus 60 to move horizontally, a control panel 58 for controlling the horizontal moving means, and an operating unit 59 for controlling the position of the hyperthermo-radiative apparatus 60. Further, the horizontal moving means includes a motor 55 installed on one side of the mat for hot compress and acupressure, a pulley 54 connected directly with the motor 55, and a rope 52 for transmitting driving force from the motor 55 to the hyperthermo-radiative apparatus 60 through the pulley 54. Here, the mat for hot compress and acupressure is covered with a mat cloth (not shown) that can sufficiently cover the longitudinal groove located at the center of the mat. Thus, the external appearance of the mat can be protected and the hyperthermo-radiative apparatus 60 can be prevented from coming into direct contact with a vertebral region of a user.

Furthermore, the conventional hyperthermo-radiative apparatus 60 that has been used in the mat for hot compress and acupressure is schematically shown in FIG. 1B. That is, the conventional hyperthermo-radiative apparatus 60 comprises a supporting stand 61 fixed to a supporting plate 56 for supporting the entire portion of the apparatus, a lamp 62 installed on the supporting stand 61, and a cap 65 for transferring heat generated from the lamp 62 and protecting the lamp 62. Here, the cap 65 is constructed in such a manner that an upper portion thereof is hemispherical, a central portion thereof is hollow cylindrical, and a lower portion thereof is provided with an outwardly flared flange 66. The upper portion of the cap is formed with a plurality of small holes 67 to emit the heat.

Therefore, when a user who wishes to obtain the effects of the hot compress and acupressure intends to utilize the conventional mat for hot compress and acupressure constructed as such, the user first lies down on the mat and presses down a button on the operating unit 59. Then, the motor 55 is actuated during a time when the button continues to be pressed down. Thereafter, the hyperthermo-radiative apparatus 60 is pulled through the pulleys 53, 54 and the rope 52, and is conveyed horizontally on the rails 51 in a longitudinal direction. When the hyperthermo-radiative apparatus 60 is completely moved to one side of the rails 51, a reverse switch (not shown) installed on a distal end of the rails 51 causes the flow direction of current applied to the motor 55 to be changed in the opposite flow direction. Thus, the hyperthermo-radiative apparatus 60 comes to stop temporarily, changes its direction of movement, and then moves again in the opposite direction. That is, at least while the user presses down the button on the operating unit 59, the hyperthermo-radiative apparatus 60 advances completely in one direction and then in the opposite direction again. During the horizontal movement, the hyperthermo-radiative apparatus 60 emits the heat from the lamp 62 installed therein, and the heat reaches the vertebral region of the user through the small holes 67. Consequently, a hot compress effect can be obtained. At the same time, while the hemispherical cap 65 located at an uppermost end of the hyperthermo-radiative apparatus 60 moves along the rails 51 in a straight line, the vertebral region of the user lying down on the mat is caused to (et acupressure in the straight line.

However, in case of the conventional mat for hot compress and acupressure, while the hyperthermo-radiative apparatus 60 is moved, the cap 65 should be moved in a state where it is pressed down by the vertebral region of the user lying down on the mat for hot compress and acupressure. Thus, friction resistance is generated in the mat cloth (not shown) positioned between the user and the hyperthermo-radiative apparatus, and causes the protective cloth to be easily damaged. In addition, the user feels a pain on his/her vertebral region due to the friction resistance. Further, it was difficult to manufacture the conventional hyperthermo-radiative apparatus 60 since the protective cap 65 thereof should be machined in the form of the hemisphere. The difficulty in manufacturing the apparatus was aggravated since the cap was made thinner in order to accomplish more rapid heat transfer.

Furthermore, the conventional mat for hot compress and acupressure has required more power in moving the hyperthermo-radiative apparatus 60 due to friction resistance between the user and the hyperthermo-radiative apparatus 60. Consequently, the large motor for generating high driving force was used, and thus, consumption of unnecessary electric power was incurred. In addition, when the hyperthermo-radiative apparatus 60 is moved in the conventional mat for hot compress and acupressure, excessive load is produced due to the friction resistance. If the load cannot be overcome, the rope 52 slips onto the pulley 53. Thus, there was a problem in that the hyperthermo-radiative apparatus 60 cannot be normally moved.

SUMMARY OF THE INVENTION

Therefore, the present invention is conceived to solve the aforementioned problems in the prior art and is directed to a new type hyperthermo-radiative apparatus for use in a mat for hot compress and acupressure.

An object of the present invention is to provide a roller type hyperthermo-radiative apparatus, which can minimize friction resistance generated when the apparatus moves horizontally within a central portion of the mat for hot compress and acupressure.

Another object of the present invention is to provide a roller type hyperthermo-radiative apparatus, which can enhance effects of the hot compress and acupressure on a user According to an aspect of the present invention for achieving the objects, there is provided a roller type hyperthermo-radiative apparatus, a backing plate with wheels fixedly supported at four corners thereof; a plurality of pairs of supporting means mounted on the backing plate; roller type rotating members rotatably installed between respective pairs of the supporting means and with cylindrical empty spaces formed therein; heating members inserted into the empty spaces of the rotating members from both ends of the spaces; socket portions connected to the heating members for supplying external electric power; and bearing members for fixedly supporting the socket portions to the supporting means and for rotatably coupling the rotating members thereto.

According to the present invention, it is preferred that the roller type rotating members of the hyperthermo-radiative apparatus for generating far infrared radiation be made of inorganic mineral, and the roller type rotating members of the hyperthermo-radiative apparatus be also formed such that outer portions thereof are smoothly curved with respect to their own rotation axes while inner portions thereof have empty cylindrical spaces. Thus, the roller type rotating members can be spontaneously rotated while moving horizontally and friction resistance of the rotating members can be greatly reduced.

Further, according to the present invention, it is preferred that the roller type hyperthermo-radiative apparatus be mounted on the mat for hot compress and acupressure and the power needed for moving the hyperthermo-radiative apparatus 100 can also be reduced.

BRIEF DESCRIPTION OF THE DRAWINGS

The above objects and features of the present invention will become apparent from the following description of preferred embodiments given in connection with the accompanying drawings, in which:

FIG. 2B is a front view of the roller type hyperthermo-radiative apparatus with the main portion thereof cut away.

FIGS. 3A to 3C show other preferred embodiments of the roller type hyperthermo-radiative apparatus 100 of the present invention, and in particular, FIG. 3A shows a V-shaped roller type hyperthermo-radiative apparatus, FIG. 3B shows a hybrid roller type hyperthermo-radiative apparatus, and FIG. 3C shows a cross roller type hyperthermo-radiative apparatus;

FIG. 5A shows a state where the roller type hyperthermo-radiative apparatus approaches toward curved portions of curved rails, FIG. 5B shows a state where a general roller type hyperthermo-radiative apparatus approaches and ascends the curved portions of the curved rails, and FIG. 5C shows a state where the V-shaped roller type hyperthermo-radiative apparatus approaches and ascends the curved portions of the curved rails.

DETAILED DESCRIPTION OF THE INVENTION

Hereinafter, preferred embodiments of the present invention will be described in detail with reference to the accompanying drawings.

The present invention is directed to a roller type hyperthermo-radiative apparatus 100 for a mat for hot compress and acupressure.

Figure 2A:
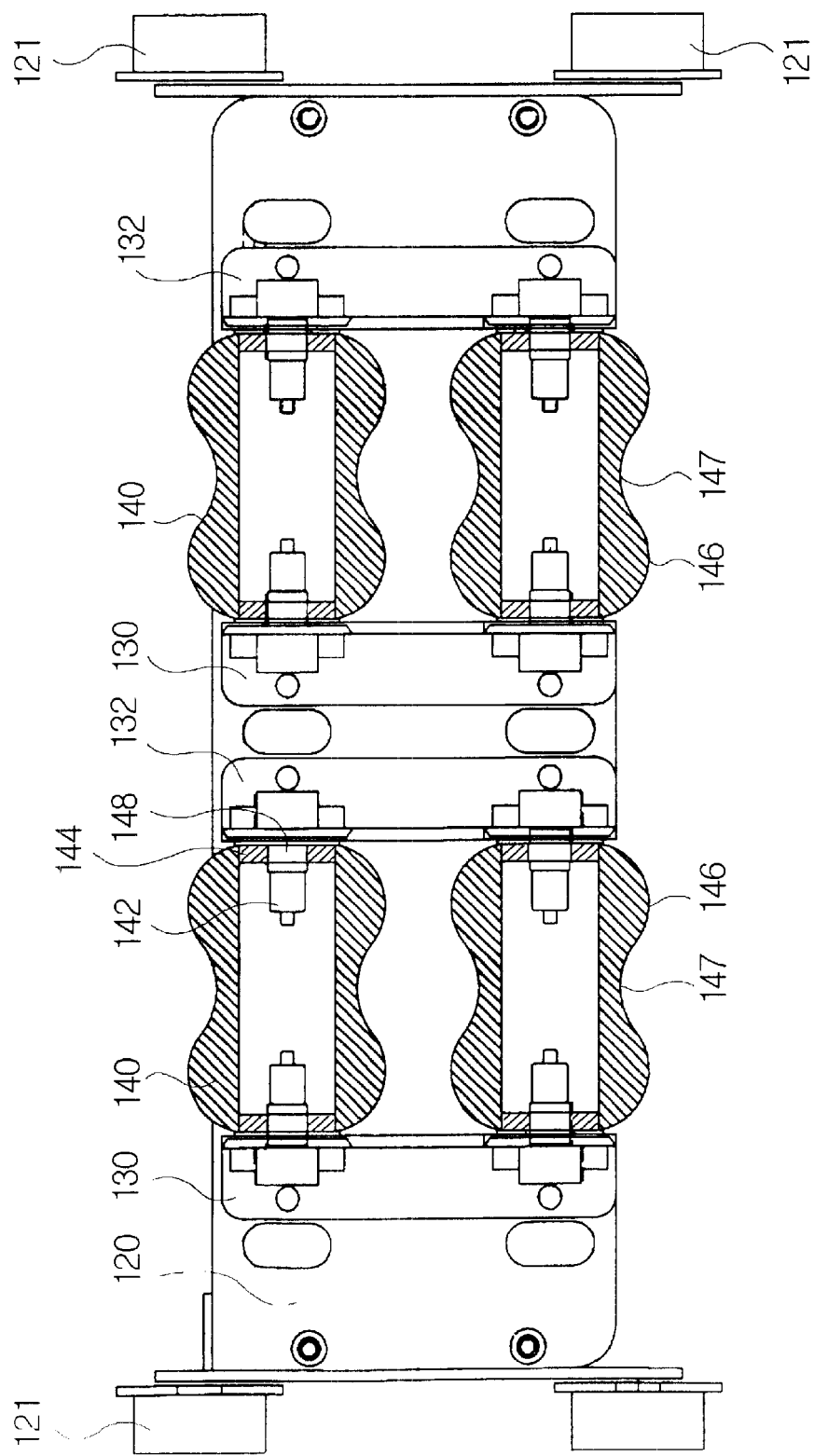
FIG. 2A is a plan view of the roller type hyperthermo-radiative apparatus of the present invention, with a main portion thereof cut away.
Figure 2C:
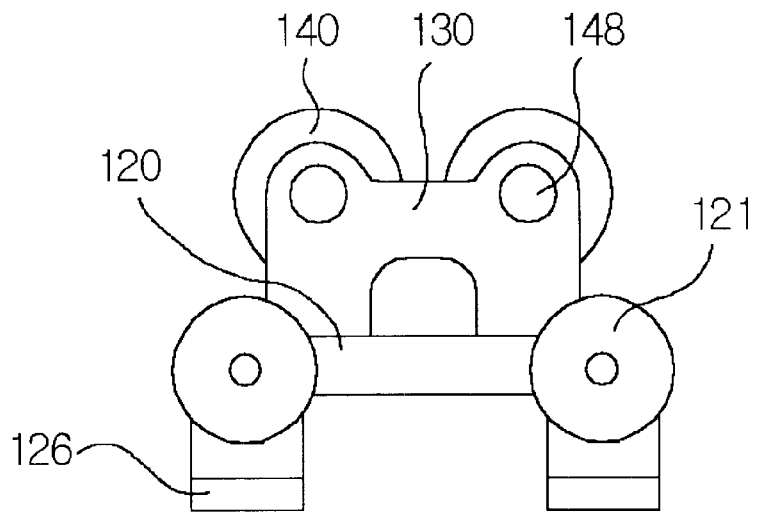
FIG. 2C is a left side view of the roller type hyperthermo-radiative apparatus.

FIG. 2A its a plan view of the roller type hyperthermo-radiative apparatus 100, as viewed from above, with rotating members cut away; FIG. 2B is a front view of the roller type hyperthermo-radiative apparatus 100, with the rotating members cut away; and FIG. 3C is a left side view of the roller type hyperthermo-radiative apparatus 100. The roller type hyperthermo-radiative apparatus 100 of the present invention comprises a backing plate 120 with wheels 121 that move along rails 220 installed in the central space of the mat for hot compress and acupressure. The backing plate 120 comprises a plurality of pairs of supporting means 130, 132 that are installed to be opposed to each other on a plane thereof. The backing plate 120 is provided with connecting members 124 for coupling the plate with the conveying means, at front and rear central portions thereof. Further, the plate 120 is provided with the wheels 121 and flanges 126 disposed below the wheels, at four corners thereof. Since the flanges 126 are fitted below the rails 220, the flanges allow the roller type hyperthermo-radiative apparatus 100 to move stably and prevent the apparatus from running off the rails 220 when the wheels 121 of the apparatus roll on the rails 220. The hyperthermo-radiative apparatus 100 of the present invention includes roller type rotating members 140 between the plurality of pairs of the supporting means 130, 132. The rotating members 140 are rotatably installed between the supporting means 130, 132. A cylindrical empty space where heating members 142 inserted from both ends of the space are accommodated is formed within the interior of the rotating member 140. When the hyperthermo-radiative apparatus 100 moves while coming into contact with a body of the user, the rotating members 140 rotate on their own axes while exerting slight pressure on the body of the user. Thus, friction resistance of the rotating members can be greatly reduced, and the power needed for moving the hyperthermo-radiative apparatus 100 can also be reduced. Further, it is preferred that the rotating members 140 be made of an inorganic mineral from which the far infrared radiation can be emitted. The reason is that in order to improve the effects of the present invention, the rotating members 140 should provide the user's region to be treated with an acupressure effect and also emit the far infrared radiation thereto. In the present invention, it is preferred that the inorganic mineral be comprised of jade as a major composition. It is also preferred that the rotating members 140 be formed with external surfaces thereof being curved, in order to improve the acupressure effect on the body of the user. That is, the external surfaces may comprise peak portions 146 which protrude toward the outside, and valley portions 147 which are relatively indented. In such a case, since the peak portions 146 exert the slight pressure on the body of the user, the acupressure effect on the user can be further enhanced. On the other hand, heat is generated from the heating members 142 by an external power source. When high temperature heat is emitted, the heat is transferred to the body of the user and the far infrared radiation is also emitted from the rotating members 140. In the present invention, it is preferred that infrared lamps be used as the heating members 142. Preferably, the heating members 142 are not rotated unlike the roller type rotating members 140, and they are fixedly installed. To this end, it is preferred that bearing members 144 be positioned and used between the socket portions 148 and the roller type rotating members 140. The bearing members 144 may be constructed in such a manner that inner rings thereof are coupled with the socket portions 148 whereas outer rings thereof are coupled with the rotating members 140. Furthermore, the socket portions 148 also perform a function of transferring the external electric power to the heating members 142. Herein, the hyperthermo-radiative apparatus as described above and as shown in FIGS. 2A to 2C will be referred to as a "general roller type hyperthermo-radiative apparatus".

Figure 3A:
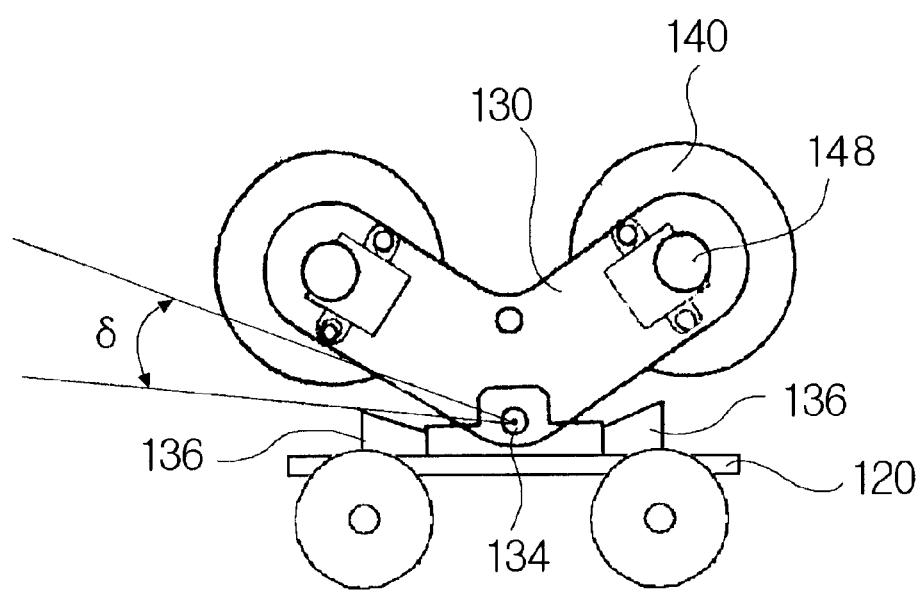
Figure 3C:
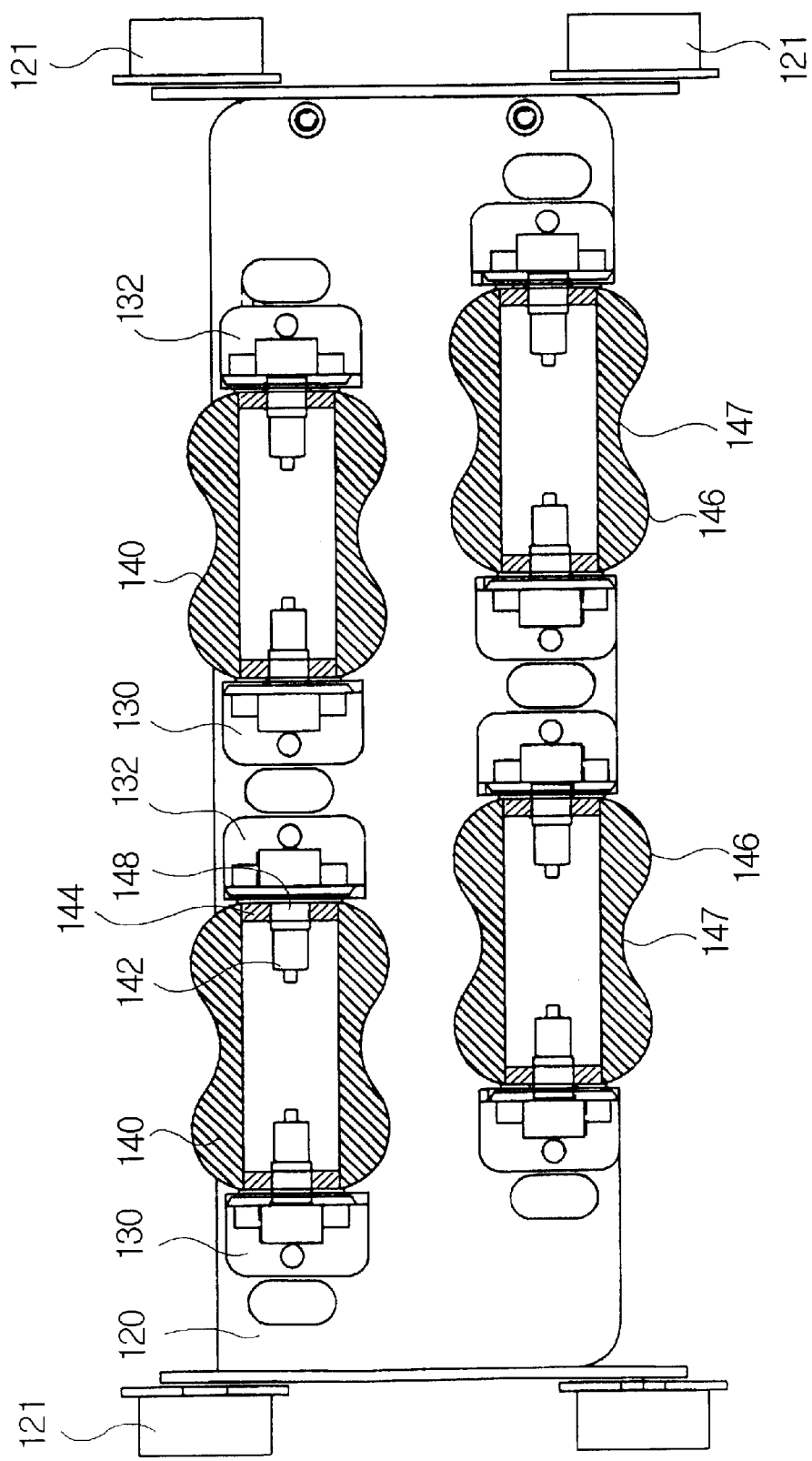

FIGS. 3A to 3C show other preferred embodiments of the roller type hyperthermo-radiative apparatus 100 according to the present invention, respectively. FIG. 3A is a side view showing one of the preferred embodiments of the roller type hyperthermo-radiative apparatus 100 according to the present invention wherein the supporting means 130, 132 are further improved. In the present invention, the supporting means 130, 132 be preferred constructed in a V shape. It is preferred that a shaft 134 be formed at a lower vertex of the V-shaped supporting means 130, 132 to perform a function of hinge with respect to the backing plate 120. Further, stoppers 136 are formed on the backing plate 120 disposed below the V-shaped supporting means 130, 132, and thus, the supporting means 130, 132 can be prevented from slanting excessively toward either side. It is preferred that the stoppers 136 be made of elastic material in order to reduce impact. On the other hand, an angle formed between the V-shaped supporting means 130, 132 and the stopper 136 with respect to the shaft 134 as a vertex is 6 which greatly correlates with an angle α formed between the horizontal plane and curved portions 222, 224 of the curved rails 220. Herein, the hyperthermo-radiative apparatus in which the V-shaped supporting means 130, 132 and the hinge shafts 134 are formed will be referred to as a "V-shaped roller type hyperthermo-radiative apparatus". In particular, the V-shaped roller type hyperthermo-radiative apparatus call be usefully employed in the curved rails 220 having the curved portions 222, 224.

Figure 1A:
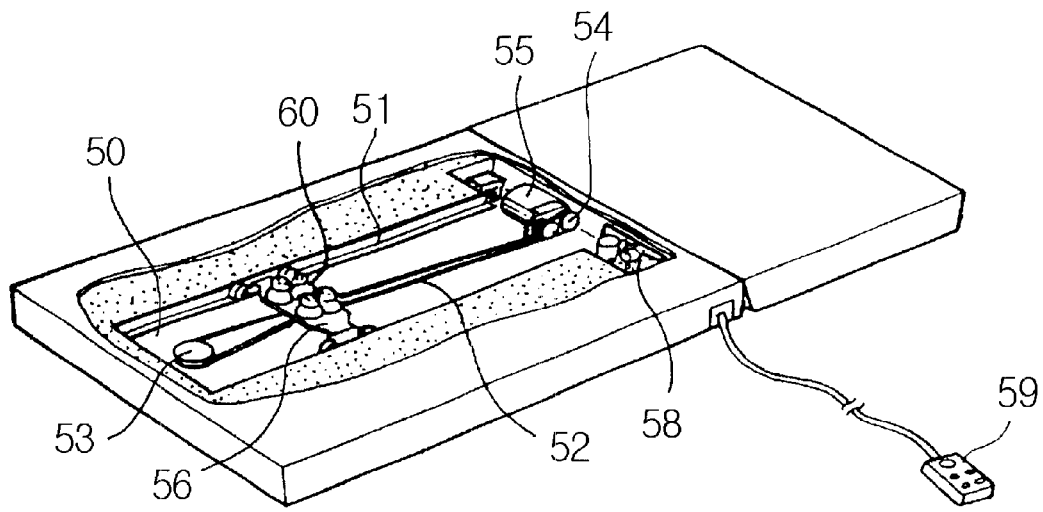
FIGS. 1A and 1B show a conventional mat for hot compress and acupressure and a conventional hyperthermo-radiative apparatus, respectively.
Figure 1B:
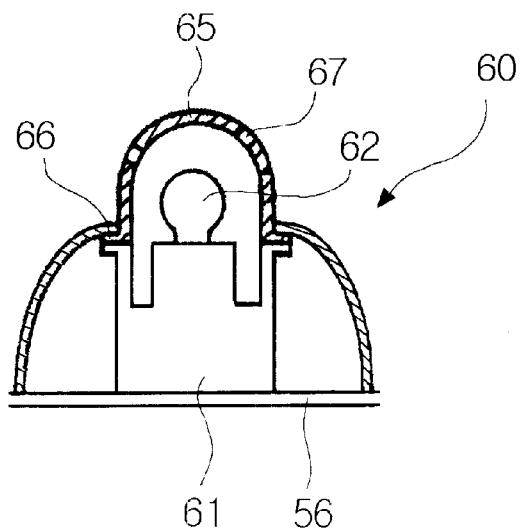

FIG. 3B shows one of other preferred embodiments of the roller type hyperthermo-radiative apparatus 100 according to the present invention wherein the conventional hyperthermo-radiative apparatus 60 is further provided in a space between the plurality of the rotating members 140. The conventional hyperthermo-radiative apparatus 60 has the same basic construction as shown in FIG. 1B and is fixed to the backing plate 120. It is also preferred that the hyperthermo-radiative apparatus 60 be installed in the empty space formed between the rotating members 140. Herein, the hyperthermo-radiative apparatus in which the new hyperthermo-radiative apparatus with the roller type rotating members used therein is employed together with the conventional hyperthermo-radiative apparatus will be referred to as a "hybrid roller type hyperthermo-radiative apparatus". Since the mat 200 according to the present invention comprises the hybrid roller type hyperthermo-radiative apparatus, the rotating members 140 and the conventional hyperthermo-radiative apparatus 60 of the hybrid roller type hyperthermo-radiative apparatus can emit the far infrared radiation evenly to the user's body.

FIG. 3C shows a further preferred embodiment of the roller type hyperthermo-radiative apparatus 100 according to the present invention, wherein each of rotating members 140 are slightly staggered with respect to one another. Here, it is sufficient that the supporting means 130, 132 are slightly staggered laterally with respect to the advancing direction of the hyperthermo-radiative apparatus, or they are manufactured in the form of "V" in which the supporting means are slightly bent laterally with respect to the advancing direction of the hyperthermo-radiative apparatus. In this case, the rotating members 140 can emit the far infrared radiation evenly to the user's body in the advancing direction thereof. Further, since the curved peak portion 146 is placed to be followed by the valley portion 147 of the next rotating member 140 in the advancing direction, the number of portions for exerting acupressure on the user increases as large as the number of the peak portions 146. Thus, more excellent acupressure effect can be obtained. In such case, there is no need for additional installation of the conventional hyperthermo-radiative apparatus 60 in the empty space between the rotating members 140, as shown in FIG. 3B. Herein, such hyperthermo-radiative apparatus in which the roller type rotating members are staggered with respect to one another will be referred to as a "cross roller type hyperthermo-radiative apparatus." In the present invention, insofar the roller type hyperthermo-radiative apparatus 100 is not specifically defined, it is intended to include all of the general roller type hyperthermo-radiative apparatus, V-shaped roller type hyperthermo-radiative apparatus, hybrid roller type hyperthermo-radiative apparatus and the cross roller type hyperthermo-radiative apparatus, which are described in detail above and illustrated in FIGS. 3A to 3C.

The roller type hyperthermo-radiative apparatus 100 according to the present invention can be essentially mounted on the mat for hot compress and acupressure 200.

Figure 4A:
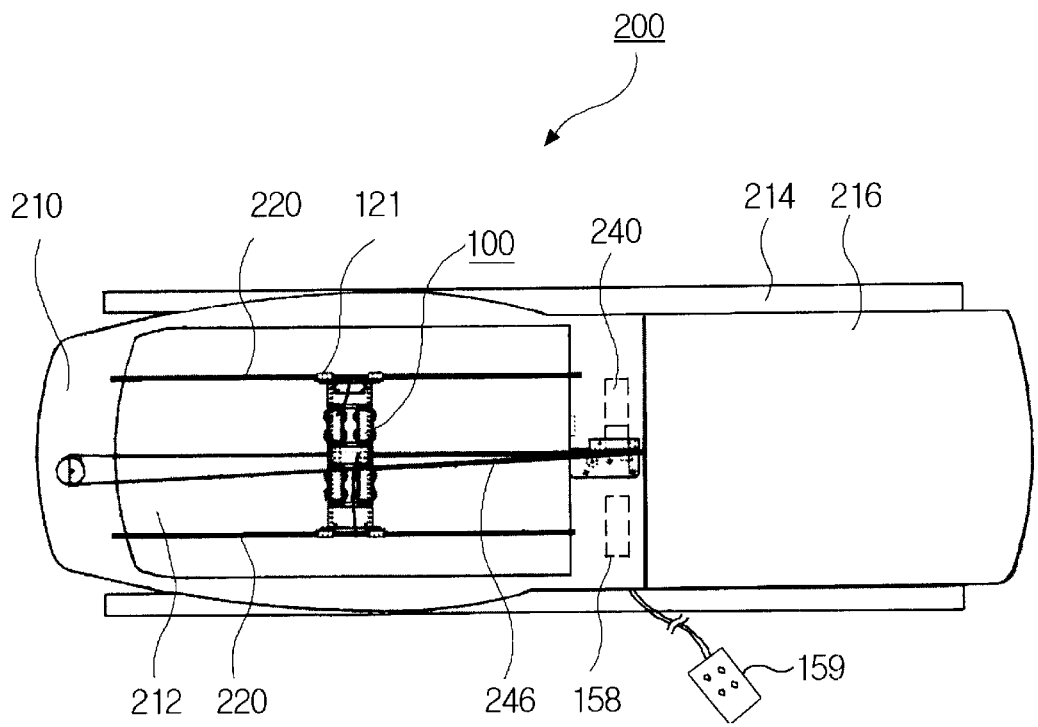
FIG. 4A is a plan view of a mat for hot compress and acupressure 200 according to a preferred embodiment of the present invention as viewed from above.
Figure 4B:
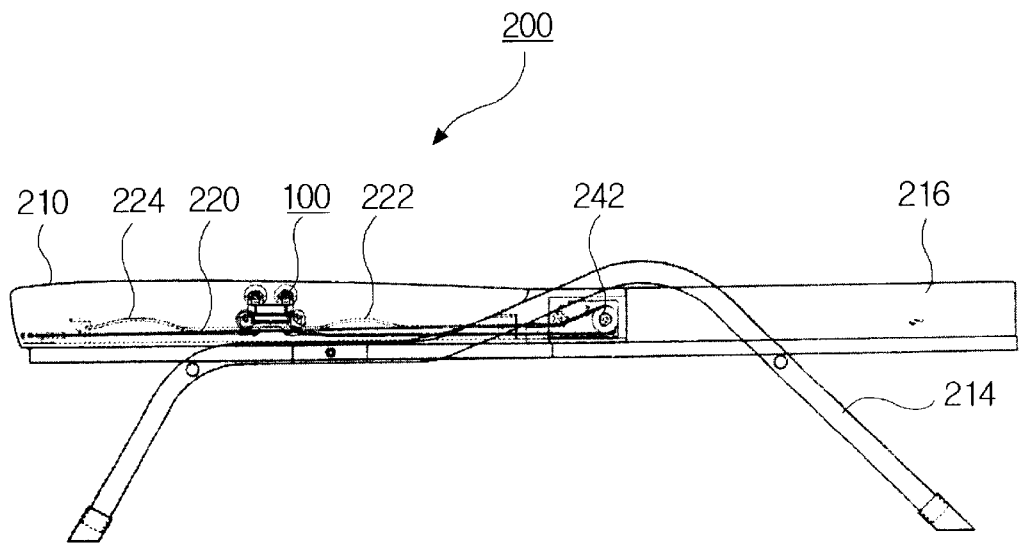
FIG. 4B is a front view of the mat for hot compress and acupressure 200.
Figure 5A:
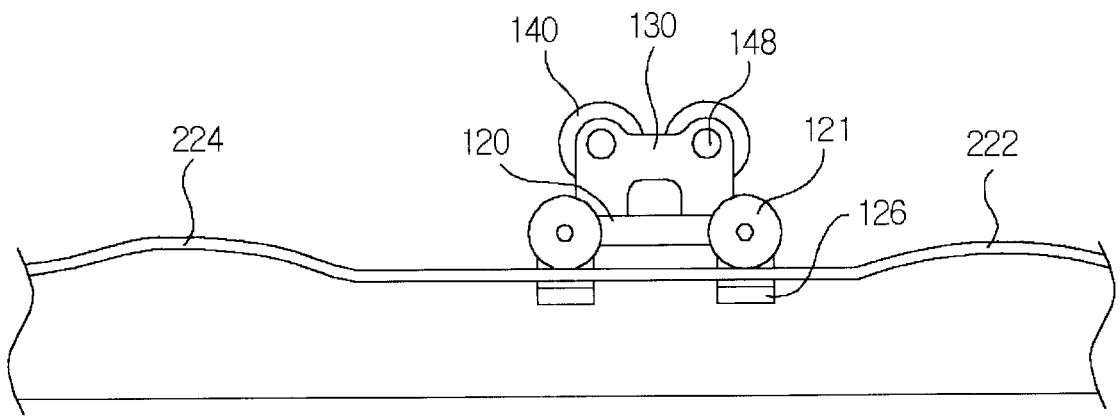
FIGS. 5A to 5C are conceptual views for schematically showing the interrelationship between the roller type hyperthermo-radiative apparatus and the curved rails, and in particular.
Figure 5B:
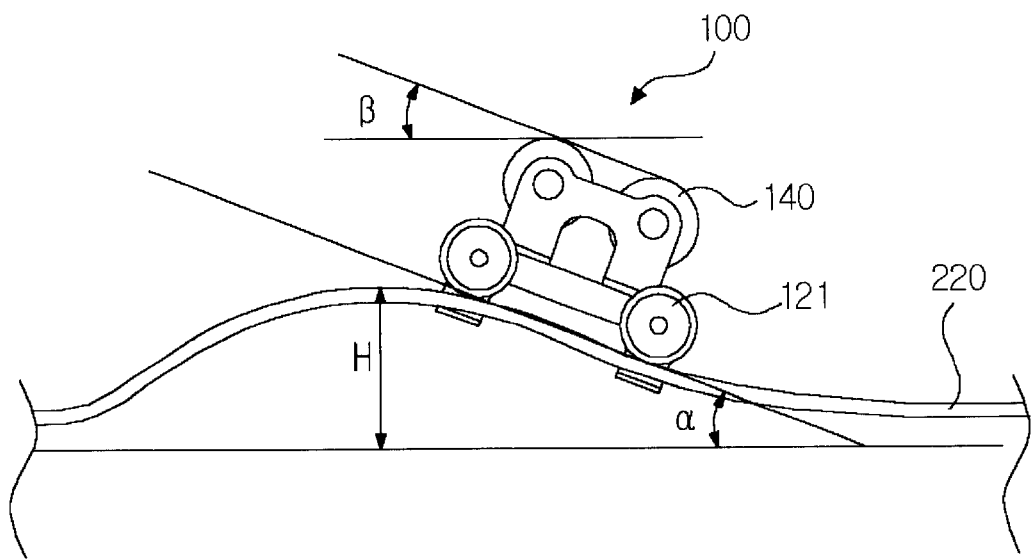
Figure 5C:
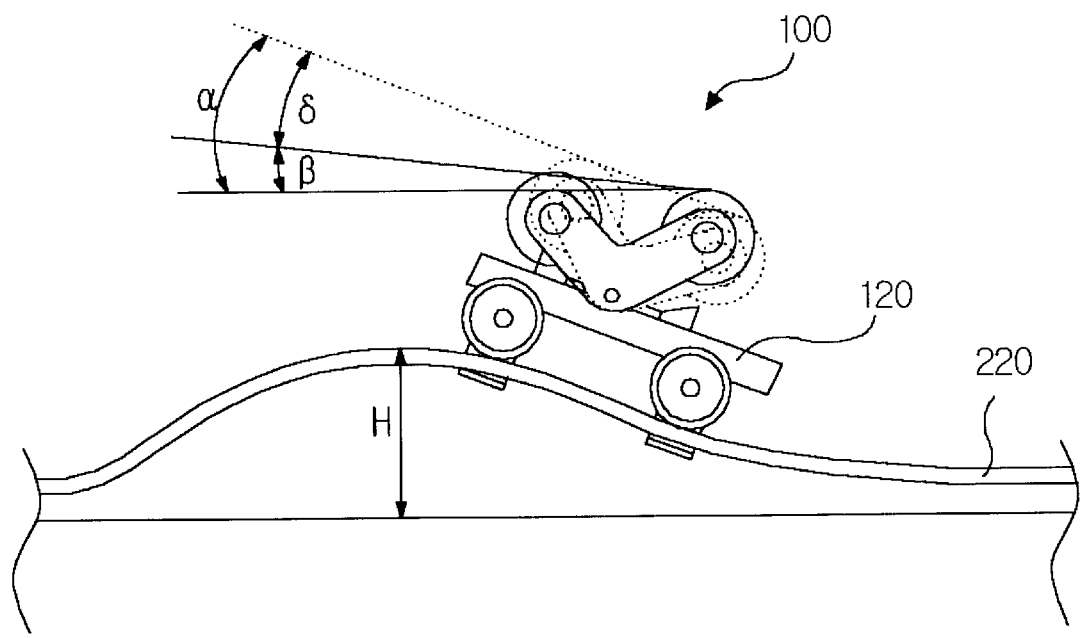

FIG. 4A is a plan view of the mat for hot compress and acupressure 200, and FIG. 4B is a front view of the mat for hot compress and acupressure 200. The mat for hot compress and acupressure 200 may comprise a mat member 210 with a longitudinal groove 212 formed in the center thereof, and another mat member 216 electrically connected to and foldable toward the mat member 210. The mat for hot compress and acupressure 200 may comprise curved rails 220 formed at both sides of the central groove 212 on the bottom of the mat member 210 and with curved portions corresponding to the curvature of the vertebral region of a user. The longitudinal groove 212 formed in the center of the mat member 210 provides a space for accommodating essential components of the present invention. The mat for hot compress and acupressure 200 may essentially comprise the roller type hyperthermo-radiative apparatus 100 traveling along the curved rails 220. The mat for hot compress and acupressure 200 may comprise the conveying means for moving the roller type hyperthermo-radiative apparatus 100 in a horizontal direction. The mat for hot compress and acupressure 200 may comprise a control panel 158 for controlling the conveying means and an operating unit 159 for adjusting a position of the roller type hyperthermo-radiative apparatus 100. In use, the mat members 210, 216 can be mounted onto a frame body 214 with prefabricated legs FIGS. 5A to 5C are conceptual views for schematically showing the interrelationship between the roller type hyperthermo-radiative apparatus 100 according to the present invention and the curved rails 220. The mat for the hot compress and acupressure 200 includes the respective curved rails 220 at both sides of the longitudinal groove 212 on the bottom of the mat. Each curved rail 220 includes the curved portion 222 corresponding to the curvature of the lumbar vertebral region of the user, and the curved portion 224 corresponding to the nape region of the neck of the user. Since the lumbar vertebral region and the nape region of the neck of the user are not flattened but slightly curved upwardly when the user lies down on the mat, the curved portions 222, 224 are designed to uniformly exert the hot compress and acupressure even on the lumbar vertebral region and the nape region of the neck of the user by raising the roller type hyperthermo-radiative apparatus 100 at the lumbar vertebral region and the nape region of the neck of the user in accordance with the curved portions 222, 224 of the rails. At this time, it is preferred that the curved portions 222, 224 be formed to slope somewhat gently. The degree of gentle slope may have an interrelationship depending on the roller type hyperthermo-radiative apparatus 100 according to the present invention (see FIGS. 5A to 5C).

FIG. 5A shows a state where the roller type hyperthermo-radiative apparatus 100 of the present invention approaches toward the curved portions of the curved rails. FIG. 5B shows a state where the general roller type hyperthermo-radiative apparatus of the present invention approaches and ascends the curved portion 222. FIG. 5C shows a state where the V-shaped roller type hyperthermo-radiative apparatus of the present invention approaches and ascends the curved portion 222. Assuming that the angle formed between the general roller type hyperthermo-radiative apparatus 100 and the horizontal plane at a position where the general roller type hyperthermo-radiative apparatus 100 ascends the curved portion is α (alpha) in FIG. 5B, the angle actually formed between the horizontal plane (the vertebral region of the user) and the two rotating members 140 becomes β (beta). At this time, as for the general roller type hyperthermo-radiative apparatus 100 according to the present invention, the angles α and β are identical to each other. Therefore, in a case where the general roller type hyperthermo-radiative apparatus 100 of the present invention is employed in the mat for the hot compress and acupressure, as the angle α is set smaller, the pressure exerted on the vertebral region of the user who lies down on the mat is lowered. Accordingly, it is preferable to set the angle α smaller. However, if the angle α is set smaller, the height H generated by the curved portions 222, 224 is lowered. Thus, it is difficult to sufficiently obtain its acupressure effects to the necked and the vertebral region of the user. In order to overcome the conflict therebetween, there is an urgent need for a method of reducing the angle β while increasing the angle α. In order to meet the need, the V-shaped roller type hyperthermo-radiative apparatus 100 according to the present invention is employed in FIG. 5C.

In FIG. 5C, when the V-shaped roller type hyperthermo-radiative apparatus 100 of the present invention ascends the curved portions 222, 224, the angle formed between the horizontal plane and the backing plate 120 is α, whereas the angle formed between the horizontal plane and the two rotating members 140 is β. At this time, the angle β is always smaller than the angle α. This is because the two rotating members 140 have a tendency that they intend to be in the horizontal state by means of the hinge shaft 134 by being subjected to the same weight of the user. This tendency is naturally generated in the range of angle δ formed between the V-shaped supporting means 130, 132 and the stoppers 136. Here, the angle δ corresponds to a value obtained by subtracting the angle δ from the angle α. If the V-shaped roller type hyperthermo-radiative apparatus 100 is manufactured such that the angle α is identical to the angle δ, the angle β is zero. Thus, even if the V-shaped roller type hyperthermo-radiative apparatus 100 according to the present invention ascends the curved portions 222, 224, the rotating members 140 can continuously remain in the horizontal state, so that the user receives relatively smaller pressure from the rotating members 140 and the friction resistance generated between the user and the rotating members 140 is relatively reduced. This is true not only when the V-shaped roller type hyperthermo-radiative apparatus 100 ascends the curved portions 222, 224 but also when it descends the curved portions. Therefore, it is preferred that the angle δ be set to be larger than zero but equal to or smaller than the angle α.

The mat 200 with the roller type hyperthermo-radiative apparatus 100 of the present invention operates as follows. After the user turns on the power source for the mat, he/she manipulates the operating unit 159 while lying down on the mat. Then, the electric power is supplied to the heating member 142 which in turn is turned on. In order to move the roller type hyperthermo-radiative apparatus 100, if necessary, a motor 240 is rotated. Accordingly, the roller type hyperthermo-radiative apparatus 100 can be smoothly moved by the conveying means forward or rearward without any slippage. During such procedure, the rotating members 140 of the roller type hyperthermo-radiative apparatus 100 of the present invention perform acupressure with respect to and transfer heat to the vertebral acupressure points of the user, so that the far infrared radiation penetrates into the vertebral region of the user. Further, as the roller type hyperthermo-radiative apparatus 100 according to the present invention advances, the rotating members 140 are pushed down due to the weight of the user and thus smoothly rotated. This rotation imparts only rolling resistance, resulting in reduced friction resistance. Consequently, the power needed for the pulling of the roller type hyperthermo-radiative apparatus 100 is lowered as compared with a conventional one. Thus, the mat for hot compress and acupressure 200 can employ a low-power motor, and thus, waste of the electric power can be prevented. In addition, the sizes of operating portions can be reduced, resulting in compactness of the mat for hot compress and acupressure 200. Furthermore, noise can be reduced in operation.

Although the preferred embodiments of the roller type hyperthermo-radiative apparatus according to the present invention have been described with reference to the accompanying drawings, the present invention is not limited thereto. It is apparent that various changes and modifications may be made thereto by those skilled in the art without departing from the spirit and scope of the invention as defined by the appended claims.

What is claimed is:

1. A roller type hyperthermo-radiative apparatus for a mat for hot compress and acupressure, comprising:
   a) a backing plate with wheels fixedly supported at four corners thereof;
   b) a plurality of pairs of supporting means mounted on the backing plate;
   c) roller type rotating members rotatably installed between respective pairs of the supporting means and with cylindrical empty spaces formed therein;
   d) heating members inserted into the empty spaces of the rotating members from both ends of the spaces;
   e) socket portions connected to the heating members for supplying external electric power; and
   f) bearing members for fixedly supporting the socket portions to the supporting means and for rotatably coupling the rotating members thereof.

2. The roller type hyperthermo-radiative apparatus as claimed in claim 1, wherein the backing plate is provided with connecting members for coupling the plate with conveying means, at front and rear central portions thereof.

3. The roller type hyperthermo-radiative apparatus as claimed in claim 2, wherein the backing plate is further provided with the wheels and flanges disposed below the wheels, at four corners thereof.

4. The roller type hyperthermo-radiative apparatus as claimed in claim 3, wherein the roller type rotating members are comprised of an inorganic mineral containing jade as a major composition.

5. The roller type hyperthermo-radiative apparatus as claimed in claim 4, wherein each of the roller type rotating members includes outwardly protruding peak portions and a relatively indented valley portion.

6. The roller type hyperthermo-radiative apparatus as claimed in claim 5, wherein the supporting means are constructed in a V-shape and a shaft is formed at a lower vertex of the V-shaped supporting means to perform a function of hinge with respect to the backing plate.

7. The roller type hyperthermo-radiative apparatus as claimed in claim 6, wherein the backing plate includes stoppers thereon.

8. The roller type hyperthermo-radiative apparatus as claimed in claim 7, wherein the stoppers are made of elastic material.

9. The roller type hyperthermo-radiative apparatus as claimed in claim 4, wherein each of the rotating members are slightly staggered with respect to one another.

10. The roller type hyperthermo-radiative apparatus as claimed in claim 5, wherein a space between the rotating members is employed together with the conventional hyperthermo-radiative apparatus.

11. The roller type hyperthermo-radiative apparatus as claimed in claim 5, wherein each of the rotating members are slightly staggered with respect to one.

12. The roller type hyperthermo-radiative apparatus as claimed in claim 6, wherein a space between the rotating members is employed together with the conventional hyperthermo-radiative apparatus.

13. The roller type hyperthermo-radiative apparatus as claimed in claim 6, wherein each of the rotating members are slightly staggered with respect to one another.

14. The roller type hyperthermo-radiative apparatus as claimed in claim 7, wherein a space between the rotating members is employed together with the conventional hyperthermo-radiative apparatus.

15. The roller type hyperthermo-radiative apparatus as claimed in claim 7, wherein each of the rotating members are slightly staggered with respect to one another.

* * * * *